United States Patent [19]

Vasta

[11] Patent Number: 4,531,010

[45] Date of Patent: Jul. 23, 1985

[54] ESTER CURING AGENT FOR FLUOROCARBON POLYMER COATING COMPOSITION

[75] Inventor: Joseph A. Vasta, Wilmington, Del.

[73] Assignee: E. I. Du Pont de Nemours and Company, Wilmington, Del.

[21] Appl. No.: 566,996

[22] Filed: Dec. 30, 1983

Related U.S. Application Data

[62] Division of Ser. No. 509,705, Jun. 30, 1983.

[51] Int. Cl.³ .................. C07C 101/24; C07C 101/26
[52] U.S. Cl. ..................... 560/125; 560/116; 560/117; 560/118; 560/119; 560/120; 560/121; 560/123; 560/124; 560/169; 525/326.3; 525/381
[58] Field of Search ............... 560/125, 169, 116, 117, 560/118, 119, 120, 121, 123, 124

[56] References Cited

U.S. PATENT DOCUMENTS

| | | | |
|---|---|---|---|
| 2,979,418 | 4/1961 | Dipner | 117/72 |
| 3,093,264 | 6/1963 | Harris | 220/63 |
| 3,337,609 | 8/1967 | Williamson et al. | 560/169 |
| 3,366,612 | 1/1968 | Baldwin et al. | 260/85.3 |
| 3,526,532 | 9/1970 | Heiberger | 117/75 |
| 3,558,345 | 1/1971 | Baum et al. | 117/54 |
| 3,692,558 | 9/1972 | Werner | 117/72 |
| 3,824,115 | 7/1974 | Segawa et al. | 117/21 |
| 3,850,674 | 11/1974 | Clarke, Jr. et al. | 117/76 T |
| 3,955,036 | 5/1976 | Plueddemann | 428/429 |
| 3,988,502 | 10/1976 | Patel et al. | 526/18 |
| 4,035,565 | 7/1977 | Apotheker et al. | 526/249 |
| 4,170,686 | 10/1979 | Miller et al. | 428/416 |
| 4,179,542 | 12/1979 | Christofas et al. | 428/324 |
| 4,180,487 | 12/1979 | Floyd | 560/169 |
| 4,237,177 | 12/1980 | Slama et al. | 428/215 |
| 4,284,755 | 8/1981 | Lohse et al. | 560/169 |
| 4,298,416 | 11/1981 | Casson et al. | 156/87 |
| 4,299,869 | 11/1981 | Casson et al. | 428/35 |
| 4,307,142 | 12/1981 | Blitstein et al. | 428/143 |
| 4,323,603 | 4/1982 | Close | 524/545 |
| 4,343,841 | 8/1982 | Close | 427/386 |
| 4,347,277 | 8/1982 | Slama et al. | 428/215 |

OTHER PUBLICATIONS

Bulletin No. 78C-15 by Abbott Laboratories, Industrial Amines, pp. 1–3.
Du Pont Sales Brochure—Viton ® Fluoroelastomers.
Abstract from Official Gazette, Aug. 23, 1983, p. 1602—U.S. Pat. No. 4,400,482.

*Primary Examiner*—Natalie Trousof
*Assistant Examiner*—Patricia M. Scott
*Attorney, Agent, or Firm*—Hilmar L. Fricke

[57] ABSTRACT

A curing agent for fluorocarbon polymer coating compositions having the formula

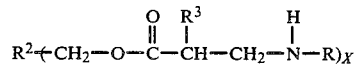

where R is $R^1NH$, $R^1$ is an aliphatic or cycloaliphatic hydrocarbon radical, $R^2$ is C or an aliphatic hydrocarbon group, $R^3$ is H or $CH_3$, where x is 3 when $R^2$ is a hydrocarbon group and x is 4 when $R^2$ is C; the curing agents form ambient curing fluorocarbon polymer coating compositions;

These compositions are used to provide corrosion and abrasion resistant coatings for large structures in chemical plants, oil refineries, oil drilling platforms, and the interior of smoke stacks of large utility companies.

6 Claims, No Drawings

ESTER CURING AGENT FOR FLUOROCARBON POLYMER COATING COMPOSITION

CROSS REFERENCE TO RELATED APPLICATIONS

This application is a divisional application of Ser. No. 509,705 filed June 30, 1983.

BACKGROUND OF THE INVENTION

This invention is related to a curing agent and in particular to a curing agent for a fluorocarbon polymer coating composition.

Fluorocarbon polymers are inert to strong acids such as sulfuric acid, nitric acid, hydrochloric acid and strong bases such as sodium hydroxide and are resistant to weathering and salt water corrosion and are tough and abrasion resistant. Coatings of these polymers would be useful in chemical plants and oil refineries to coat pipes, vessels and other equipment, on off shore oil well platforms, on ships, and as protective coatings for the interior of smoke stacks of utility companies. Fluorocarbon polymer coatings would be particularly useful for metal smoke stack interiors which are subjected to abrasion from fly ash and corrosion by acids resulting from combustion products such as $SO_x$ and $NO_x$ and halogen ions. However, conventional fluorocarbon polymer coatings require curing at elevated temperatures which could not be used on the aforementioned structures. An ambient curing fluorocarbon polymer coating composition is required.

The curing agent of this invention is used in fluorocarbon polymer coating composition and provides a composition that cures at ambient temperatures.

SUMMARY OF THE INVENTION

An ester curing agent for fluorocarbon polymer coating compositions having the following formula:

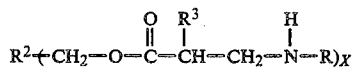

where R is $R^1NH_2$, $R^1$ is an aliphatic or cycloaliphatic hydrocarbon radical, $R^2$ is C or a hydrocarbon group, $R^3$ is H or $CH_3$; where x is 3 when $R^2$ is a hydrocarbon group and x is 4 when $R^2$ is C.

DETAILED DESCRIPTION OF THE INVENTION

The ester curing agent is prepared through a Michael's reaction in which a multifunctional acrylate or methacrylate is reacted with a polyamine. The polyamine is heated to about 100°–150° C. and then the multifunctional acrylate or methacrylate is reacted with the polyamine for a 1–6 hour period to form an amine terminated curing agent.

Typical multifunctional acrylates or methacrylates that can be used to form the curing agent are trimethylol propane acrylate, trimethylol propane methacrylate, pentaerythritol acrylate, pentaerythritol methacrylate and the like.

Typical polyamines used to form the curing agent are isophorone diamine which is 3-aminomethyl-3,5,5-trimethylcyclohexylamine, hexamethylene diamine, ethylene diamine, 1,4-cyclohexane bis(methylamine), 1,2-diaminopropane, propylene diamine, diethyl ether diamine, trimethylhexamethyl methylene diamine and the like.

The curing agent is used in fluorocarbon polymer coating compositions or primer compositions. Generally, about 5–25% by weight, based on the weight of the binder of the composition, of curing agent is used.

One of the advantages of compositions that contain the curing agent is that these compositions cure at ambient temperatures and baking is not required. Therefore, the compositions can be used on large structures such as chemical storage tanks, chemical reactors the interior of smoke stacks and the like which could not be subjected to baking temperatures using conventional techniques.

Typical coating compositions contain about 10–17% by weight binder and 30–90% by weight of an organic solvent, in which the binder is a fluorocarbon polymer of vinylidene fluoride and hexafluoropropylene and has a weight average molecular weight of about 50,000–300,000 and contains a metallic oxide such as magnesium oxide which is an acid acceptor.

Usually the composition contains a reinforcing pigment such as titanium dioxide or carbon black.

Molecular weight, as used herein, is determined by gel permeation chromatography using polymethylmethacrylate as a standard.

Preferably, the polymer used in the coating composition contains about 50–70% by weight of vinylidene fluoride and 30–50% by weight of hexafluoropropylene. The polymer can contain up to 40% by weight of other monomers such as tetrafluoroethylene. One useful polymer contains about 20–30% by weight of tetrafluoroethylene;.

The metallic oxide which is an acid acceptor is used in the composition to react with the hydrofluoric acid which is generated during the curing or crosslinking reaction. Typical metallic oxides are magnesium oxide, lead oxide, calcium oxide, lead hydrogen phosphite and a mixture of calcium oxide and magnesium oxide. Magnesium oxide is preferred.

Generally, the binder of a coating composition contains about 55–90% by weight, of the fluorocarbon polymer, 5–25% by weight of one of the above amine curing agents and 5–20% by weight of a metallic oxide which is an acid acceptor.

The coating composition also can contain dispersed fluorocarbon polymers such as polytetrafluoroethylene, fluorinated ethylene/propylene polymers, polyvinyl fluoride, polyvinylidene fluoride, copolymer of tetrafluoroethylene/perfluoroalkoxy vinyl ether and the like. These dispersed fluorocarbon polymers are present in amounts of about 5–20% by weight, based on the weight of the binder of the composition.

Preferably, the coating composition contains a reinforcing agent such as titanium dioxide pigment usually in a pigment to binder weight ratio of about 20:100 to 200:100. Other inert pigments can be used such as barytes, barium sulfate, fibrous calcium silicate and the like. Carbon black, bone black or lamp black can also be used as a reinforcing pigment in a pigment to binder weight ratio of about 20:100 to 50:100.

Typical organic solvents that are used in the coating composition are acetone, tetrahydrofuran, methyl ethyl ketone, ethyl acetate, propyl acetate, butyl acetate, isobutyl acetate, methyl isobutyl ketone, methyl amyl acetate, diisobutyl ketone, ethylene glycol monomethyl ether acetate, ethylene glycol monoethyl ether and mixtures of the above. These solvents are used to make the compositions and can be used to reduce the compositions to an application viscosity.

To decrease curing time and increase toughness of the resulting finish of the coating composition about 0.01-3% by weight based on the weight of the binder, of a bicyclic amidine can be added. One preferred bicyclyic amidine is 1,8-diaza-bicyclo(5,4,0)undecene-7.

Generally, the coating composition is sold in two components. The solvents, fluorocarbon polymer, pigments such as titanium dioxide and metallic oxide acid acceptor are the first component and the amine curing agent is the second component. The second component is blended with the first component by the user to form a coating composition. The composition is then reduced with one of the aforementioned solvents to an application viscosity and then applied to a substrate.

The coating composition can be applied directly over a wide variety of substrates and provide a fluorocarbon polymer coating. Typical substrates are treated or primed steel, phosphatized steel, grit blasted steel, galvanized steel, aluminum, copper, brass, cement and cementitious surfaces such as fire brick, mortar used for fire brick and the like.

Generally, the coating composition is sprayed applied to the substrate and the solvent is allowed to flash off between coatings then the resulting coating composition is cured at ambient temperatures. The coating can be cured in about 4 to 48 hours or longer or can be heated to 80° C. to 120° C. for 0.5 to 2.0 hours for rapid curing. Cured coatings are about 75-1500 microns thick.

For some substrates such as untreated steel, a fluorocarbon primer is first applied and then while the primer is still wet the coating composition is applied and dried at ambient temperatures or at the above elevated temperatures.

One useful primer contains the aforementioned fluorocarbon polymer, a metallic oxide acid acceptor such as magnesium oxide and an aminoalkyl-alkoxy silane such as amino-propyl trimethoxysilane or amino-propyl triethoxysilane.

The ambient curing characteristics of the coating composition provided by the novel amine curing agent of this invention allows for the application of coatings on large vessels and reactors in chemical plants, and oil refineries, large structures and equipment and pipes, heat risers, i.e., pipes which are used to transport oil from the underground well to the structure, off shore oil well platforms, and on the interior of smoke stacks used by large utility companies. It is practical to use compositions that cure at ambient temperature for the above applications.

The following examples illustrate the invention. All parts and percentages are on a weight basis unless otherwise indicated.

EXAMPLE

The following amine curing agents were prepared:

| | CURING AGENT Parts by Weight | | | |
|---|---|---|---|---|
| | D | E | F | G |
| Isophorone diamine | 510 | — | 562 | — |
| Hexamethylene diamine | — | 321 | — | 388 |
| Trimethylol propane aerylate | 296 | 296 | — | — |
| Pentaerythritol acrylate | — | — | 298 | 298 |

-continued

| | CURING AGENT Parts by Weight | | | |
|---|---|---|---|---|
| | D | E | F | G |
| Isopropanol | 659 | 505 | 703 | 562 |
| Total | 1465 | 1122 | 1563 | 1248 |

In the preparation of each of the above curing agents D-G, the amine was charged into a reaction vessel and heated to 120°-140° C. and then the acrylate was slowly added at a uniform rate over a 4 hour period and then the reaction mixture was cooled and isopropanol added.

Trimethylol propane acrylate and pentaerythritol acrylate were prepared by conventional techniques well known to the skilled in the art in which an acrylate moiety was attached to trimethylol propane and to pentaerythritol.

Separate coating compositions were prepared with each of the curing agents D-G. About 5 parts of the curing agent was added to about 300 parts of the following coating composition:

Fluorocarbon polymer solution containing 33% solids in ethyl acetate of a copolymer of 40% hexafluoropropylene and 60% vinylidine fluoride having a weight average molecular weight of about 100,000 and about 5% by weight magnesium oxide. In each case the resulting coating composition was reduced to a spray viscosity with methyl ethyl ketone and sprayed onto grit blasted steel panels allowing the coating to flash dry between each application to provide a 1000 micron thick dry coating. After 7 days, the coatings were fully cured. The coatings were resistant to sulfuric acid, sodium hydroxide and methyl ethyl ketone.

I claim:

1. A curing agent for fluorocarbon polymers consisting of

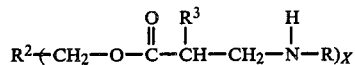

where R is $R^1NH_2$, $R^1$ is an aliphatic or cycloaliphatic hydrocarbon radical, $R^2$ is C or hydrocarbon group, $R^3$ is H or $CH_3$, where x is 3 when $R^2$ is a hydrocarbon group and x is 4 when $R^2$ is C.

2. The curing agent of claim 1 in which $R^1$ is an aliphatic hydrocarbon radical.

3. The curing agent of claim 2 in which $R^1$ is $-(CH_2)_6-$.

4. The curing agent of claim 1 in which $R^1$ is a cycloaliphatic hydrocarbon radical.

5. A curing agent having the formula

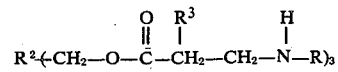

where $R^2$ is a hydrocarbon group having up to and including three carbon atoms and R is

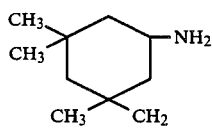

6. A curing agent having the formula
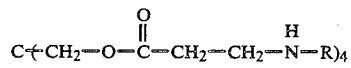
where R is
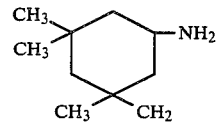
* * * * *